United States Patent [19]

Yotsuya et al.

[11] Patent Number: 4,894,790
[45] Date of Patent: Jan. 16, 1990

[54] INPUT METHOD FOR REFERENCE PRINTED CIRCUIT BOARD ASSEMBLY DATA TO AN IMAGE PROCESSING PRINTED CIRCUIT BOARD ASSEMBLY AUTOMATIC INSPECTION APPARATUS

[75] Inventors: Teruhisa Yotsuya; Hideaki Takahara, both of Kyoto, Japan

[73] Assignee: Omron Tateisi Electronics Co., Kyoto, Japan

[21] Appl. No.: 11,481

[22] Filed: Feb. 5, 1987

[30] Foreign Application Priority Data

Feb. 5, 1986 [JP] Japan .................................. 61-23294
Feb. 14, 1986 [JP] Japan .................................. 61-31719

[51] Int. Cl.$^4$ ......................... G06F 7/02; G06F 15/20; G01N 21/88; G01N 21/91
[52] U.S. Cl. ................................... 364/552; 364/491; 382/8; 358/101; 358/107
[58] Field of Search ............................... 364/488–491, 364/552, 559; 382/8, 17, 30, 34; 358/101, 106, 107; 324/73 PL; 250/492.1, 492.2

[56] References Cited

U.S. PATENT DOCUMENTS

| | | | |
|---|---|---|---|
| 4,028,728 | 6/1977 | Sharp .................................. | 358/106 |
| 4,404,683 | 8/1983 | Kobayashi et al. ...................... | 382/6 |
| 4,450,579 | 5/1984 | Nakashima et al. .................. | 364/490 |
| 4,574,393 | 3/1986 | Blackwell et al. .................... | 382/17 |
| 4,669,123 | 5/1987 | Kobayashi et al. .................... | 382/8 |
| 4,692,690 | 9/1987 | Hara et al. ........................... | 358/101 |
| 4,764,969 | 8/1988 | Ohtombe et al. ....................... | 382/8 |
| 4,776,022 | 10/1988 | Fox et al. ............................ | 382/8 |

FOREIGN PATENT DOCUMENTS 0124113 11/1984 European Pat. Off. .
0231941 8/1987 .
2138238 2/1973 Fed. Rep. of Germany .
3314465 10/1984 Fed. Rep. of Germany .

OTHER PUBLICATIONS

Goto et al; An Automatic Inspection System for Printed Wiring Board Masks; Patern Recognition, vol. 12, pp. 443-455, 1980.

Restrick III, An Automatic Optical Printed Circuit Inspection System, Bell Laboratories, SPIE 1977.
Patent Abstracts of Japan, vol. 8, No. 165 (P-291)(1602) 31st Jul. 1984; & JP-A-59 61705 (Matsushita Denki Sangyo K.K.) 09-04-1984.
Journal of the Optical Society of America AB, vol. 3, No. 9, Sep. 1986, pp. 1465–1482, Woodbury, N.Y. US; J. L. C. Sanz et al.: "Machine-Version Techniques for Inspection of Printed Wiring Boards and Thick-Film Circuits", p. 1475.

Primary Examiner—Parshotam S. Lall
Assistant Examiner—Ellis B. Ramirez
Attorney, Agent, or Firm—Wegner & Bretschneider

[57] ABSTRACT

An apparatus for automatic inspection of printed circuit board assemblies inspects for the correct presence, positioning, and orientation of component parts mounted on a base printed circuit board by processing an image which is obtained from the base printed circuit board mounted with these component parts. In this method for inputting reference printed circuit board assembly data to such an apparatus, a reference base printed circuit board is prepared with reference component parts mounted on it in which the visual distinction between the reference base printed circuit board and these reference component parts is clear, and then an image is obtained from this reference base printed circuit board assembly, and this image is then processed in order to obtain the reference printed circuit board assembly data. Thereby laborious keying in of such reference printed circuit board assembly data is avoided, and the occurrence of errors is minimized. Optionally, the reference base printed circuit board may be arranged to have low visual brightness, while the reference component parts are arranged to have high visual brightness; or the reverse; or the reference base printed circuit board may be arranged to have substantially different color value from that of the reference component parts. The reference base printed circuit board may be made to be fluorescent, optionally by being coated with a fluorescent film, which may itself be further coated with a layer of transparent adhesive agent, which can further serve for retaining the reference component parts.

15 Claims, 6 Drawing Sheets

| LABEL 1 | POSITION X1, Y1 | SHAPE F1 |
|---|---|---|
| LABEL 2 | POSITION X2, Y2 | SHAPE F2 |
|  |  |  |
| LABEL n | POSITION Xn, Yn | SHAPE Fn |

FIG. 7
PRIOR ART

INPUT METHOD FOR REFERENCE PRINTED CIRCUIT BOARD ASSEMBLY DATA TO AN IMAGE PROCESSING PRINTED CIRCUIT BOARD ASSEMBLY AUTOMATIC INSPECTION APPARATUS

BACKGROUND OF THE INVENTION

The present invention relates to a method for inputting reference printed circuit board data to an apparatus for automatic inspection of printed circuit board assemblies which checks such printed circuit board assemblies for any omissions or mis-placements of component parts by processing a picture image thereof, and more particularly relates to such a method for inputting reference printed circuit board assembly data to such an automatic inspection apparatus, wherein such data are inputted from a reference or sample printed circuit board assembly rather than piecemeal as individual data, i.e. are inputted by example rather than directly.

In the prior art, there have been proposed various types of method for inputting reference printed circuit board assembly data to such an automatic printed circuit board assembly inspection machine. That is to say, when an automatic printed circuit board component mounting machine is used for mounting various component parts such as micro chips, other semiconductor devices, resistors, capacitors, and the like to an empty or bare printed circuit board in order to prepare a printed circuit board assembly ready for suffering a soldering process, it is possible that in an individual instance not all the component parts will be properly assembled to the bare printed circuit board according to the required arrangement therefore. Therefore an inspection or checking process is required to be performed for verifying that all the component parts are properly assembled to the bare printed circuit board, after such an automatic printed circuit board component mounting machine has completed its job of thus mounting the various component parts to said bare printed circuit board, so as to ensure that all of the components are indeed mounted to the bare printed circuit board at correct positions thereon and in their correct orientations, and for verifying that there is no omission of any such component parts. And, if such an inspection process is conducted manually by a human operator, it is not possible to completely eliminate the possibility of error, and further the speed of inspection is necessarily slow, thus hindering productivity and raising final cost of the assembly. Accordingly, lately, various types of automatic printed circuit board assembly inspection machine have been proposed for performing such an inspection process automatically. Such an automatic printed circuit board assembly inspection machine of course requires, before it can perform and fulfill its inspection function, data to be inputted to it for specifying the correct numbers, types, positions, and orientations of the parts to be fitted to a bare printed circuit board to constitute the printed circuit board assembly which said automatic printed circuit board assembly inspection machine is intended to inspect (such data will hereinafter in this specification be termed reference printed circuit board assembly data), as well as requiring input of the basic parameters of the bare printed circuit board itself.

Now, an exemplary such prior art automatic printed circuit board assembly inspection machine, and the method of inputting reference printed circuit board assembly data thereto and the method of subsequent operation of said automatic printed circuit board assembly inspection machine, will be explained with regard to FIGS. 7 through 9 of the appended drawings.

Figure 7:
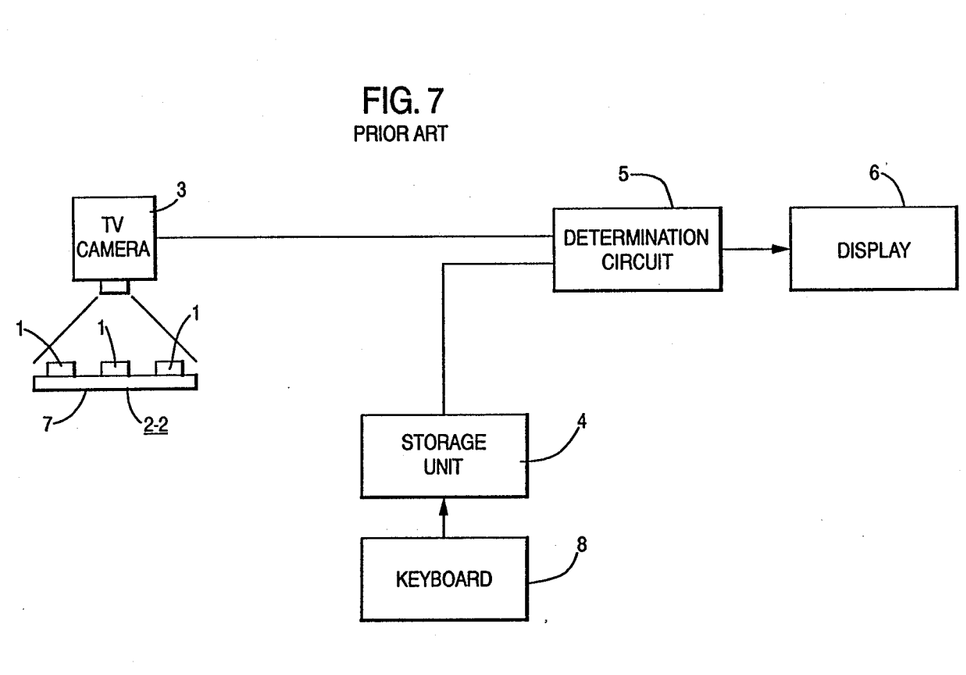
FIG. 7 is a schematic block diagram showing the overall construction of a prior art type automatic printed circuit board assembly inspection machine.
Figure 8:
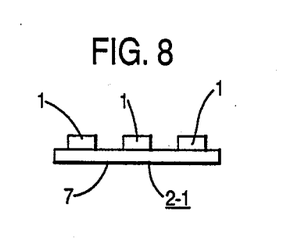
FIG. 8 is a schematic sectional view showing a reference printed circuit board assembly such as is suitable for consultation while inputting data to the prior art type automatic printed circuit board assembly inspection machine of FIG. 7.

In FIG. 7, there is shown an automatic printed circuit board assembly inspection machine according to the prior art, which comprises: a TV camera 3 for forming an image of a subject printed circuit board assembly 2—2; a storage unit 4 for storing reference printed circuit board data which are inputted from a keyboard 8, or in other words the specification of the correct numbers, types, positions, and orientations of the component parts (schematically denoted by the reference symbols 1) to be fitted to empty printed circuit boards 7 to constitute the printed circuit board assemblies 2—2 which are required to be checked and inspected (the so called "subject" printed circuit board assemblies), as well as basic data relating to the type subject printed circuit board assemblies 2—2 which are to be processed and also data relating to the inspection procedure which is to be employed; a determination circuit 5 for comparing the data stored in the storage unit 4 with the data which are indicated by the picture transmitted by the TV camera 3 and for determining whether or not agreement exists therebetween, in other words whether or not all the parts 1 are indeed correctly fitted to the subject printed circuit board assembly 2—2 in the appropriate positions and orientations; and a display unit 6 for displaying the results of the determination thus made by the determination circuit 5.

Thus, before inspecting any subject printed circuit board assemblies 2—2, it is required to input data into the storage unit 4 for specifying the correct numbers, types, positions, and orientations of the component parts 1 to be fitted to a empty printed circuit board 7 for making up such a subject printed circuit board assembly 2—2, for specifying the type of base printed circuit board 7 itself, and for specifying parameters of the inspection procedure. This so called reference printed circuit board data is inputted via the keyboard 8 in a so called teaching process, by following a schematic flow chart such as shown exemplarily in FIG. 9. This teaching process is performed while making reference to a reference printed circuit board assembly such as the reference printed circuit board assembly 2—1 exemplarily shown in FIG. 8 which consists of a bare printed circuit board 7 with the appropriate components 1 fitted thereto in the appropriate positions and orientations, said reference printed circuit board assembly 2—1 thus being intended to serve as a model for all the subject printed circuit board assemblies 2—2 which are to be inspected and checked. This teaching process routine will now be explained, with reference to FIG. 9.

Figure 9:
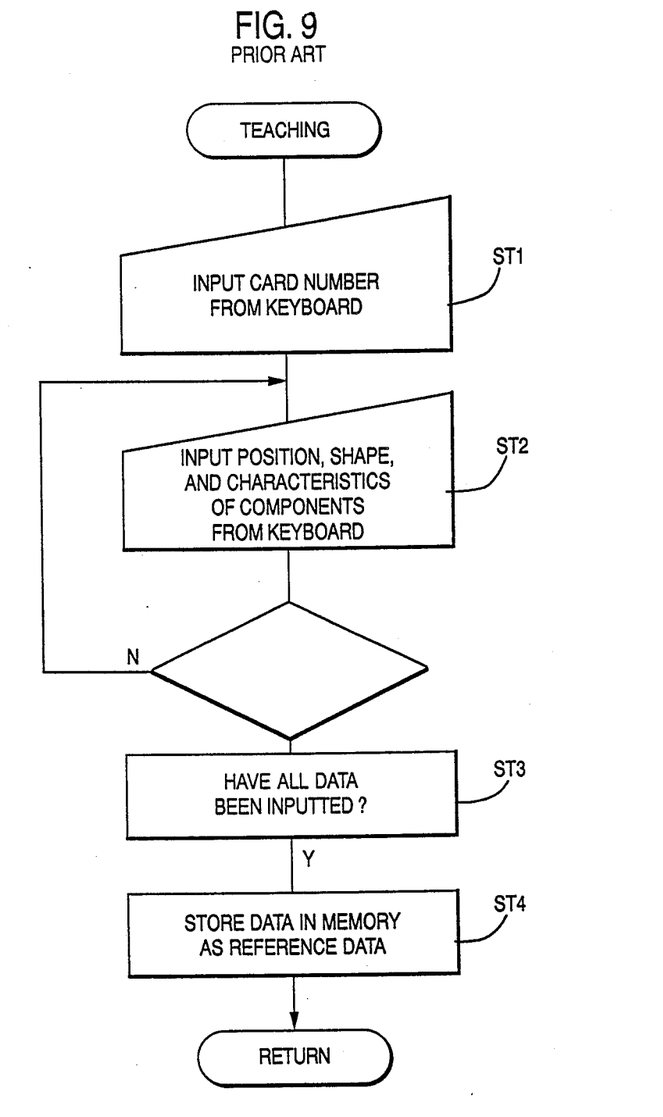
FIG. 9 is a partial flow chart for illustrating the operation of said prior art type automatic printed circuit board assembly inspection machine of FIG. 7.

First, in the first step ST1 of the FIG. 9 flow chart, the card number of the bare printed circuit board 7 of this reference printed circuit board assembly 2—1 is inputted to the storage unit 4 via the keyboard 8, and then the flow of control passes next to the step ST2.

In this next step ST2, numerical data relating to the correct type, position, and orientation of a one of the component parts 1 to be fitted to the empty printed circuit board 7 for making up the subject printed circuit board assembly 2—2 is inputted from the keyboard 8, as well as information on the characteristics of such a component part such as the color, the brightness, and so thereof; and then the flow of control passes next to the decision step ST3.

In this decision step ST3, a decision is made as to whether or not all of the data relating to all of the component parts 1 to be fitted to the empty printed circuit board 7 for making up the subject printed circuit board assembly 2—2 has yet been inputted. If the result of this decision is YES, so that all required data has now been inputted and is now available, then the flow of control passes next to the step ST4; but, if the result of this decision is NO, so that further data remains to be inputted, then the flow of control passes next to the step ST2 again, to cycle around once more and to input further data via the keyboard 8.

In the step ST4, at which point the input of all the required data has been completed, then the inputted numerical data are all stored in the storage unit 4, to constitute reference data relating to the reference printed circuit board assembly 2—1, and then the flow of control passes next to exit this teaching routine, without doing anything further.

Next, the process of inspection of a subject printed circuit board assembly 2—2 such as the one exemplarily shown in FIG. 7 will be described. When such a subject printed circuit board assembly 2—2 is presented for inspection, the determination circuit 5 compares the numerical data obtained from the picture image of said subject printed circuit board assembly 2—2 produced by the TV camera 3 with the numerical data outputted from the storage unit 4, and the results of this comparison are shown on the display unit 6. Thus, if any one of the component parts 1 which should be present on said subject printed circuit board assembly 2—2 is in fact missing or improperly positioned or is mis-aligned or is mis-oriented, there will be a disagreement between said numerical data obtained from the picture image of said subject printed circuit board assembly 2—2 produced by the TV camera 3 and said numerical data outputted from the storage unit 4, and this disagreement will be detected by the determination circuit 5 and will be signalized upon the display unit 6, along with an indication of the nature of the discrepancy, i.e. along with an indication of which part is missing, is misplaced, is mis-aligned, or is mis-oriented.

With such a method for inputting reference printed circuit board data, when an attempt is made to increase the precision of inspection by increasing the number of numerical data which serve as reference data for the inspection process, the number of such reference data that are required to be inputted from the keyboard 8 during the teaching process of FIG. 9 becomes greater and greater, and this makes the time and labor for inputting such reference data excessive. Thus, this can lead to inefficiency and delays in production, and further the possibility of error is increased beyond an acceptable level.

SUMMARY OF THE INVENTION

Thus, a desire has arisen for a method of automatically inputting such reference data, and this has therefore motivated the inventors of the present invention to consider the various problems detailed above.

Accordingly, it is the primary object of the present invention to provide a method for inputting reference printed circuit board assembly data, which avoids the problems detailed above.

It is a further object of the present invention to provide such a method for inputting reference printed circuit board assembly data, which can input in a rapid and efficient manner data relating to the correct type, position, and orientation of the various component parts which are to be fitted to each empty printed circuit board for making up each subject printed circuit board assembly.

It is a further object of the present invention to provide such a method for inputting reference printed circuit board assembly data, which can input such reference printed circuit board assembly data without any requirement for entering such data on a keyboard.

It is a further object of the present invention to provide such a method for inputting reference printed circuit board assembly data, which can reduce the time and labor required to input such reference printed circuit board assembly data.

It is a further object of the present invention to provide such a method for inputting reference printed circuit board assembly data, which can reduce the occurrence of error during the process of inputting of such reference printed circuit board assembly data.

It is further object of the present invention to provide such a method for inputting reference printed circuit board assembly data, which can input such reference printed circuit board assembly data by example rather than directly.

It is a further object of the present invention to provide such a method for inputting reference printed circuit board assembly data, which can allow for high precision of inspection without creating severe inputting problems for said reference printed circuit board assembly data.

It is a further object of the present invention to provide such a method for inputting reference printed circuit board assembly data, which maximizes operational efficiency and promptitude.

It is a further object of the present invention to provide such a method for inputting reference printed circuit board assembly data, which utilizes inexpensive parts.

According to the most general aspect of the present invention, these and other objects are attained by a method, in an apparatus for automatic inspection of printed circuit board assemblies which inspects component parts mounted on a base printed circuit board by processing an image which is obtained from said base printed circuit board mounted with said component parts, for inputting reference printed circuit board assembly data, comprising the steps of: preparing a reference base printed circuit board with reference component parts mounted thereon in which the visual distinction between said reference base printed circuit board and said reference component parts is clear; and: obtaining an image from said reference base printed circuit board mounted with said reference component parts, and processing said image to obtain said reference printed circuit board assembly data.

According to such a method for inputting reference printed circuit board assembly data as specified above, since said reference printed circuit board assembly data are inputted by only showing a reference printed circuit board assembly to the apparatus without any laborious keying in of such reference printed circuit board assembly data, the efficiency of the data input process is much improved, and the possibility of error is minimized.

According to a particular specialization of the present invention, the above and other objects may more particularly be accomplished by such a method for inputting reference printed circuit board assembly data as specified above, wherein said reference base printed circuit board is arranged to have low visual brightness, while said reference component parts are arranged to have high visual brightness. On the contrary, it is possible for said reference base printed circuit board to be arranged to have high visual brightness, while said reference component parts are arranged to have low visual brightness. Yet further, alternatively, said reference base printed circuit board may be arranged to have substantially different color value from that of said reference component parts.

In the first of the above mentioned cases, according to a more particular specialization of the present invention, the above and other objects may more particularly be accomplished by such a method for inputting reference printed circuit board assembly data as specified above, wherein said reference base printed circuit board is arranged to be substantially dark, while said reference component parts are arranged to be substantially bright; and, yet more particularly, said reference base printed circuit board may be arranged to be substantially black, while said reference component parts may be arranged to be substantially white. Or, according to an alternative more particular specialization of the present invention, in the second of the above mentioned cases, the above and other objects may alternatively particularly be accomplished by such a method for inputting reference printed circuit board assembly data as specified above, wherein said reference base printed circuit board is made to be fluorescent; and this may optionally be done by coating said reference base printed circuit board with a fluorescent film. As a further specialization of the present invention, it is possible further to coat said reference base printed circuit board with a layer of transparent adhesive agent over said layer of film; and this layer of transparent adhesive agent may further serve for retaining said reference component parts to the reference printed circuit board assembly.

BRIEF DESCRIPTION OF THE DRAWINGS

The present invention will now be described with respect to the preferred embodiments thereof, and with reference to the illustrative drawings appended hereto, which however are provided for the purposes of explanation and exemplification only, and are not intended to be limitative of the scope of the present invention in any way, since this scope is to be delimited solely by the accompanying claims. With relation to the figures, spatial terms are to be understood as referring only to the orientation on the drawing paper of the illustrations of the relevant parts, unless otherwise specified; like reference numerals, unless otherwise so specified, denote the same parts and gaps and spaces and flow chart steps and so on in the various figures relating to one preferred embodiment, and like parts and gaps and spaces and flow chart steps and so on in figures relating to different preferred embodiments; and:

FIG. 10 is a schematic block diagram of an apparatus for automatic inspection of printed circuit board assemblies which serves for the practice of the second preferred embodiment of the method for inputting reference printed circuit board assembly data of the present invention; and:

FIG. 11 is a sectional view through an exemplary reference printed circuit board assembly along with an output signal which is produced by a TV camera included in the FIG. 10 apparatus scanning said reference printed circuit board assembly, during said practice of said second preferred embodiment of the method for inputting reference printed circuit board assembly data of the present invention.

DESCRIPTION OF THE PREFERRED EMBODIMENTS

The present invention will now be described with reference to the preferred embodiments thereof, and with reference to the figures.

The First Preferred Embodiment

Figure 1:
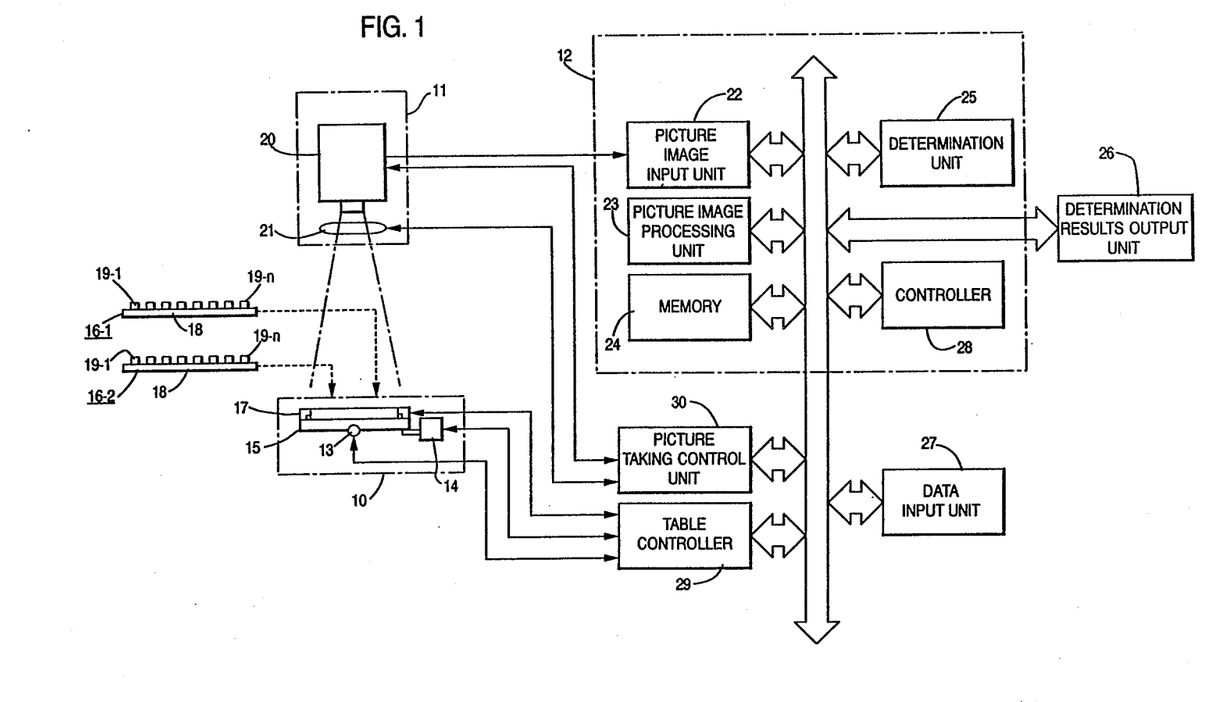
FIG. 1 is a schematic block diagram of an apparatus for automatic inspection of printed circuit board assemblies which serves for the practice of the first preferred embodiment of the method for inputting reference printed circuit board assembly data of the present invention.

FIG. 1 is a schematic block diagram of an apparatus for automatic inspection of printed circuit board assemblies which serves for the practice of the first preferred embodiment of the method for inputting reference printed circuit board assembly data of the present invention.

Construction of the apparatus

Figure 2:
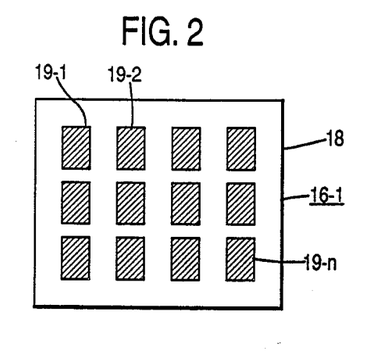
FIG. 2 is a plan view of an exemplary reference printed circuit board assembly, used in said practice of the first preferred embodiment of the present invention.

This shown apparatus for automatic inspection of printed circuit board assemblies is designed to receive a reference printed circuit board assembly 16-1 on which the distinction between the component parts thereon (designated as 19-1) and the base printed circuit board thereof (designated as 18) is particularly clear (an exemplary such reference printed circuit board assembly 16-1 is shown in FIG. 2 in plan view), and, by taking a picture image of said reference printed circuit board assembly 16-1 and processing said picture image, to input reference data relating to said reference printed circuit board assembly 16-1 for subsequently inspecting a subject printed circuit board assembly 16-2 by taking a picture thereof. And this apparatus for automatic inspection of printed circuit board assemblies comprises an X-Y table unit 10, a picture taking unit 11, a processing unit 12, a data input unit 27, a table controller 29, and a picture taking control unit 30.

The X-Y table unit 10 comprises a pair of pulse motors 13 and 14 which are controlled by the table controller 29, a table 15 which is set up so as to be driven in the X and the Y directions by these pulse motors 13 and 14 respectively, and a chuck mechanism 17 for gripping and holding first the reference printed circuit board assembly 16-1 and later the subject printed circuit board assembly 16-2, said chuck mechanism 17 being mounted on the table 15. The reference printed circuit board assembly 16-1 or the subject printed circuit board assembly 16-2 is fixed with respect to the table 15 by the chuck mechanism 17 and, after said reference or said subject printed circuit board assembly 16-1 or 16-2 has been positioned in the X and the Y directions by the pulse motors 13 and 14 respectively, the picture taking unit 11 takes a picture of said reference or said subject printed circuit board assembly 16-1 or 16-2.

In the first preferred embodiment of the method for inputting reference printed circuit board assembly data of the present invention, the reference printed circuit board assembly 16-1 is set up by painting the bare or blank base printed circuit board 18 in a bright color such as white or green or yellow or the like, by painting the side surfaces and the upper surfaces of component parts 19-1 through 19-n black or some such dark color, and by fitting said component parts 19-1 through 19-n to said base printed circuit board 18 in appropriate numbers, positions, and orientations. Thus, when the picture taking unit 11 takes a picture of the reference printed circuit board assembly 16-1, the distinction in the resultant image between said component parts 19-1 through 19-n and said base printed circuit board 18 is very clear due to this coloring arrangement.

The subject printed circuit board assembly 16-2 is a mass produced assembly, consisting (ideally and supposedly) of a base printed circuit board 18 of the same type as that utilized in the reference printed circuit board assembly 16-1, to which are fitted the same number and kinds, in the same positions and orientations, of component parts 19-1 through 19-n as the component parts 19-1 through 19-n which were fitted to said base printed circuit board 18 of said reference printed circuit board assembly 16-1. And, during the inspection process performed according to the first preferred embodiment of the method for inputting reference printed circuit board assembly data of the present invention by the apparatus for automatic inspection of printed circuit board assemblies shown in FIG. 1, the acceptability of each subject printed circuit board assembly 16-2 in turn is determined by comparing it with the reference printed circuit board assembly 16-1.

The picture taking unit 11 is mounted above the X-Y table unit 10, and comprises a TV camera 20 which is controlled by a control signal outputted from the picture taking control unit 30 so as to be properly focused and so as to provide a proper and appropriate magnification factor and sensitivity. And a ring type illumination device 21 is coaxially placed relative to this TV camera 20 and is controlled by a control signal which is outputted from the picture taking control unit 30, so as to provide an illumination level of proper and appropriate brightness. The picture signal outputted by the TV camera 20, which is an analog signal, is supplied to the processing unit 12.

First, in the so called teaching mode when the reference printed circuit board assembly 16-1 is mounted on the table 15 by the chuck mechanism 17, the processing unit 12 extracts and stores the data relating to the positions and the shapes of the component parts 19-1 through 19-n from the picture image of the reference printed circuit board assembly 16-1 which is supplied from the picture taking unit 11 and stores this data as part of the reference data relating to the characteristics of the component parts as well as the sequence of the processing. Subsequently, in the so called inspection mode when the subject printed circuit board assembly 16-2 is mounted on said table 15 by said chuck mechanism 17, the processing unit 12 extracts the data (the inspection data) relating to the positions, the shapes, and the characteristics of the component parts 19-1 through 19-n from the picture image of said subject printed circuit board assembly 16-2 which is supplied from the picture taking unit 11, and compares this inspection data with the reference data for determining the acceptability of the subject printed circuit board assembly 16-2 according to the sequence of processing. The processing unit 12 comprises a picture image input unit 22, a picture image processing unit 23, a memory 24, a determination unit 25, and a control unit 28.

The picture image input unit 22 prepares the picture image data (which is quantized data obtained after correcting the picture image signal) of the reference printed circuit board assembly 16-1 or the subject printed circuit board assembly 16-2 by analog to digital conversion of the picture image signal supplied from the picture taking unit 11 and by conducting various correction processes such as shading correction and so on or the like, and the thus obtained picture image data relating to said reference printed circuit board assembly 16-1 or said subject printed circuit board assembly 16-2 is supplied to the control unit 28 and so on.

The picture image processing unit 23 extracts various parameters, such as the areas, the shapes, the positions, and the colors, of the component parts 19-1 through 19-n which are mounted on the reference printed circuit board assembly 16-1 or the subject printed circuit board assembly 16-2 by processing the picture image data supplied from the control unit 28 according to a predetermined processing sequence or a processing sequence inputted from the data input unit 27, and the obtained parameters relating to said reference printed circuit board assembly 16-1 or said subject printed circuit board assembly 16-2 are supplied to the control unit 28.

The memory 24 stores the parameters (reference parameters) of the component parts 19-1 through 19-n which are mounted to the reference printed circuit board assembly 16-1 and the processing sequence, when they are supplied from the control unit 28, and supplies these reference parameters and so on to the picture image processing unit 23 and the determination unit 25 when such a transfer is commanded by the control unit 28.

In the inspection mode, when the subject printed circuit board assembly 16-2 is mounted to the table 15 by the chuck mechanism 17, the determination unit 25 determines whether or not any one of the component parts 19-1 through 19-n is missing or is mis-positioned on the base printed circuit board 18 of said subject printed circuit board assembly 16-2, by comparing the reference parameters outputted from the memory 24 with the parameters (the inspection parameters of said subject printed circuit board assembly 16-2), and the results of this determination are outputted to the control unit 28.

This control unit 28 controls the picture image input unit 22, the picture image processing unit 23, the memory 24, and the determination unit 25 of the processing unit 12 so that they function either in the teaching mode or in the inspection mode, and the data obtained in each of the modes are supplied to the determination results output unit 26.

This determination results output unit 26 comprises a CRT, a printer, and so on, and displays and prints out the reference parameters, the inspection parameters, the picture image data of the reference printed circuit board assembly 16-1 or the subject printed circuit board assembly 16-2, and the determination results, when such are supplied from the control unit 28.

The data input unit 27 comprises a keyboard and a mouse for inputting data relating to the type of the reference printed circuit board assembly 16-1 (such as the serial number of the base printed circuit board 18 thereof) and the kinds, the numbers, and the characteristics of the component parts 19-1 through 19-$n$ which are mounted on said reference printed circuit board assembly 16-1 and the information relating to the inputting of data, and said data input unit 27 is additionally provided with a monitor and a printer for confirming the inputted data and the information related to said inputting of the data. The data and the information related to the inputting of the data which are inputted from this data input unit 27 are supplied to the control unit 28.

The table controller 29, which comprises an interface for the control unit 28 and the X-Y table unit 10, supplies the data obtained from the X-Y table unit 10 to the control unit 28 and controls said X-Y table unit 10 according to a control signal which said table controller 29 receives from the control unit 28.

And the picture taking control unit 30, which comprises an interface for the control unit 28 and the picture taking unit 11, controls said picture taking unit 11 according to a control signal which said picture taking control unit 30 receives from the control unit 28.

Operation in The Teaching Mode

Next, the operation of this apparatus for automatic inspection of printed circuit board assemblies according to the first preferred embodiment of the method for inputting reference printed circuit board assembly data of the present invention, in the initial so called teaching mode, will be explained.

First, to initiate this so called teaching mode, the reference printed circuit board assembly 16-1 is placed on the table 15 of the X-Y table unit 10 by an operator or the like.

Next, the control unit 28 activates the chuck mechanism 17 so as to fix said reference printed circuit board assembly 16-1 to said table 15 of said X-Y table unit 10, and then said control unit 28 actuates the pulse motors 13 and 14 so as to suitably position said reference printed circuit board assembly 16-1 along the X and the Y directions, while at the same time controlling the brightness of the illumination provided by the ring type illumination device 21 and simultaneously controlling the various operational parameters of the TV camera 20.

Figure 3:
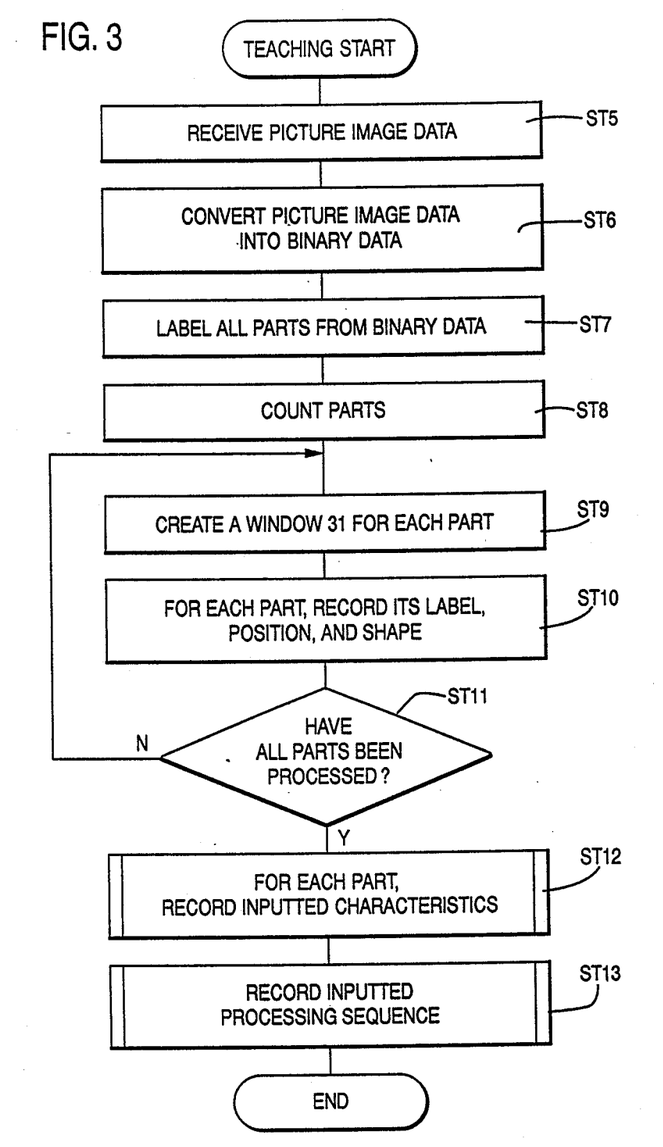
FIG. 3 is a flow chart for illustrating the operation of said first preferred embodiment of the method for inputting reference printed circuit board assembly data of the present invention, during the so called teaching phase thereof.

Thereafter, the control unit 28 commands the TV camera 20 to take a picture of the reference printed circuit board assembly 16-1, and executes the picture image processing actions a flow chart of which is shown in FIG. 3, by controlling the picture image input unit 22, the picture image processing unit 23, the memory 24, and the determination unit 25.

During this picture image processing action, the control unit 28 controls the picture image input unit 22 so as to cause it to receive the picture image signal of the reference printed circuit board assembly 16-1 obtained by the picture taking unit 11 and to prepare the picture image data of said reference printed circuit board assembly 16-1, and receives this picture image data in the step ST5.

Next, in the step ST6, said control unit 28 supplies the picture image data to the picture image processing unit 23 and converts it into a set of binary data, i.e. causes said picture image processing unit 23 to process the data in binary form, and extracts the positions and the shapes of all the component parts 19-1 through 19-$n$ contained in this picture image data; and then the flow of control passes next to the step ST7.

Next, in the step ST7, the control unit 28 takes in the positions and the shapes of the component parts 19-1 through 19-$n$ from the picture image processing unit 23, and labels (i.e. puts an identification number on) each of said component parts 19-1 through 19-$n$; and then the flow of control passes next to the step ST8.

In this case, since the reference printed circuit board assembly 16-1 is painted so that the image of these component parts 19-1 through 19-$n$ and the image of the rest of said reference printed circuit board assembly 16-1, i.e. the image of the base printed circuit board 18 thereof, are easily distinguishable from one another, thereby the positions and the shapes of these component parts 19-1 through 19-$n$ can be easily and accurately extracted when this binary processing is performed by the picture image processing unit 23.

Next, in the step ST8, the control unit 28 counts the number of the labels and obtains the number of the component parts 19-1 through 19-$n$ (which in this case is of course n), and then the flow of control passes next to the step ST9. This commences a cycle or loop which is repeated the same number of times as there are parts, i.e. n times in this case.

Figure 4:
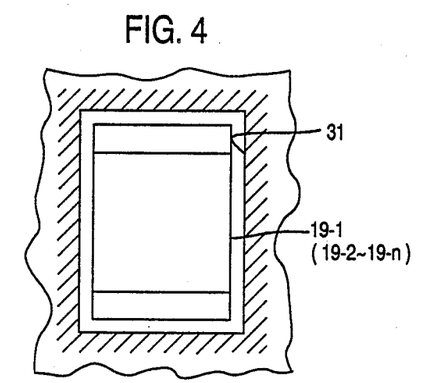
FIG. 4 is a schematic view of an exemplary window which arises during said so called teaching phase of said practice of said first preferred embodiment.

Next, in the step ST9, for each component part 19-1 through 19-$n$, a window 31 for taking in the data is created, as exemplarily shown in FIG. 4. This window 31 circumscribes the edge of the relevant component part 19-1 through 19-$n$. Then the flow of control passes next to the step ST10.

Figure 5:
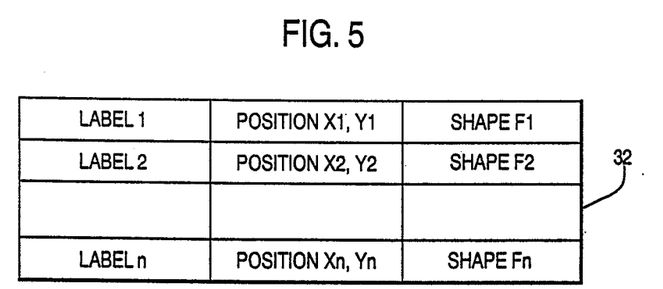
FIG. 5 is a schematic view of an exemplary file which arises during said so called teaching phase of said practice of said first preferred embodiment.

Next, in the step ST10, for each component part 19-1 through 19-$n$, the data, i.e. the label of this component part, the position thereof, and the shape thereof, (the window information) are written into a combined file 32 in the memory 24 such as exemplarily shown in FIG. 5; this file 32 is stored in the memory 24 as part of the reference data by the control unit 28. And then the flow of control passes next to the decision step ST11.

In this decision step ST11, a decision is made as to whether or not all of the component parts 19-1 through 19 $n$ have now been processed. If the result of this decision is YES, so that indeed all of said component parts 19-1 through 19-$n$ have now been processed, then the flow of control passes next to the step ST12; but, if the result of this decision is NO, so that as yet some of said component parts 19-1 through 19-$n$ remain to be processed, then the flow of control passes next back to the step ST9 again, to cycle around to process the information for the next said component part 19-1 through 19-$n$.

Next, after the reference data regarding the positions and the shapes of the component parts 19-1 through 19-$n$ have thus been stored in the memory 24, in the step ST12 the control unit 28 receives input from the data input unit 27 relating to characteristics such as color and brightness (for instance) relating to each of said component parts 19-1 through 19-$n$, and stores this data in the memory 24 as further reference data, i.e. as a characteristics data file; and then the flow of control passes next to the step ST13.

And, in this next and final step ST13 the control unit 28 receives data relating to the sequence of processing as inputted from the data input unit 27, and stores this data in the memory 24 as further reference data, i.e. as a characteristics data file; and then the flow of control passes next to leave this program fragment, without doing anything further.

This completes the description of the operation of this apparatus for automatic inspection of printed circuit board assemblies according to the first preferred embodiment of the method for inputting reference printed circuit board assembly data of the present invention, in the initial so called teaching mode.

Operation in The Inspection Mode

Next, the operation of this apparatus for automatic inspection of printed circuit board assemblies according to the first preferred embodiment of the method for inputting reference printed circuit board assembly data of the present invention, in the subsequent so called inspection mode, will be explained.

First, to initiate this so called inspection mode, the subject printed circuit board assembly 16-2 is placed on the table 15 of the X-Y table unit 10 by an operator or the like.

Next, the control unit 28 activates the chuck mechanism 17 so as to fix said subject printed circuit board assembly 16-2 to said table 15 of said X-Y table unit 10, and then said control unit 28 actuates the pulse motors 13 and 14 so as to suitably position said subject printed circuit board assembly 16-2 along the X and the Y directions, while at the same time controlling the brightness of the illumination provided by the ring type illumination device 21 and simultaneously controlling the various operational parameters of the TV camera 20.

Figure 6:
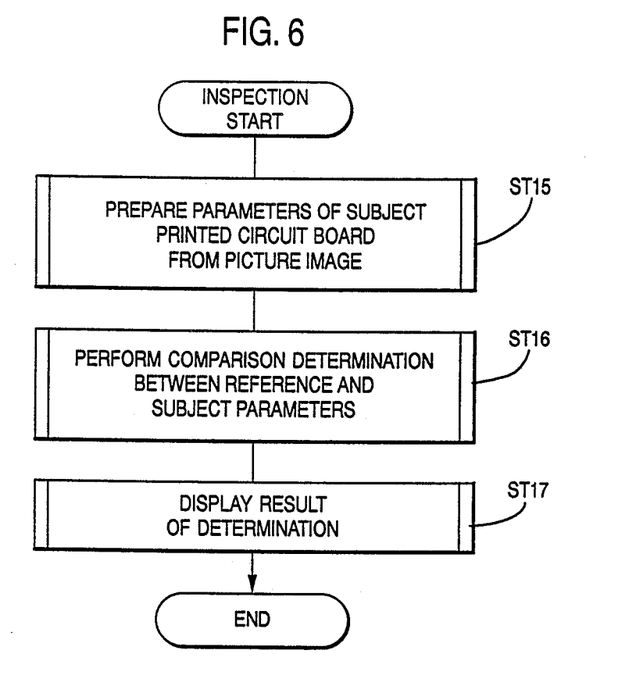
FIG. 6 is a flow chart for illustrating the operation of said first preferred embodiment of the method for inputting reference printed circuit board assembly data of the present invention, during the so called inspection phase thereof.

Thereafter, the control unit 28 commands the TV camera 20 to take a picture of the subject printed circuit board assembly 16-2, and executes the picture image processing actions a flow chart of which is shown in FIG. 6, by controlling the picture image input unit 22 to take in the picture image signal of the subject printed circuit board assembly 16-2 which was obtained by the picture taking unit 11 and to prepare the picture image data of said subject printed circuit board assembly 16-2, and receives this picture image data in the step ST15. Further, at the same time, the control unit 28 transfers the picture image data as well as the files stored in the memory 24 and the processing sequence file relating to the component parts 19-1 through 19-$n$ for the ultimate purpose of extracting the parameters (such as the colors and the brightnesses) of all of the component parts 19-1 through 19-$n$ contained in the picture image data.

Next, in the step ST16, said control unit 28 transfers all the parameters as well as the characteristic data files concerning the component parts 19-1 through 19-$n$ stored in the memory 24 to the determination unit 25 so as to cause said determination unit 25 to determine whether or not any one of said component parts 19-1 through 19-$n$ is missing or is misplaced or mis-oriented, by performing a comparison determination between the reference parameters relating to the reference printed circuit board assembly 16-1 for each of said component parts 19-1 through 19-$n$ which are given by the characteristic data files with the current inspection parameters relating to this subject printed circuit board assembly 16-2 which have been obtained from the picture image processing unit 23.

Finally, in the step ST17, the control unit 28 supplies the result of this determination to the determination results output unit 26 so as to cause said results to be displayed; and then the flow of control passes next to leave this program fragment, without doing anything further.

This completes the description of the operation of this apparatus for automatic inspection of printed circuit board assemblies according to the first preferred embodiment of the method for inputting reference printed circuit board assembly data of the present invention, in the later so called inspecting mode.

Summary of the First Preferred Embodiment

Although, according to the above described first preferred embodiment of the method for inputting reference printed circuit board assembly data of the present invention, the processing of the picture images was conducted by the picture image processing unit 23, and the determination process relating to the parameters was performed by the determination unit 25, in another possible embodiment it would be practicable for these functions to be performed by a program which was obeyed by the control unit 28.

Further, according to the above described first preferred embodiment of the method for inputting reference printed circuit board assembly data of the present invention, there was provided a window for each component part; but, in another possible embodiment, it would be feasible to provide a plurality of windows for component parts having different characteristics at their different parts, and to extract parameters for each of such windows. Alternatively, it would be possible, without using any windows, to extract the position parameters and the shape parameters for the picture image signal of the reference printed circuit board assembly 16-1 and to store them in the memory 24 as the reference data.

Thus it is seen that, according to the present invention, the data on the positions and the shapes of the component parts 19-1 through 19-$n$ fitted to the reference printed circuit board assembly 16-1 can be taught to the apparatus for automatic inspection of printed circuit board assemblies without any requirement for inputting of data relating thereto via a keyboard or the like, only by example by showing the reference printed circuit board assembly 16-1 to the apparatus for automatic inspection of printed circuit board assemblies, and accordingly not only the time required for such teaching is drastically reduced but also the labor required therefor is minimized; and further the possibility of error is greatly curtailed. Thereby, operational efficiency is maximized.

The Second Preferred Embodiment

FIGS. 10 and 11 relate to the second preferred embodiment of the method for inputting reference printed circuit board assembly data of the present invention; and, in detail, FIG. 10 shows a schematic block diagram of an apparatus for automatic inspection of printed circuit board assemblies which serves for the practice of said second preferred embodiment of the method for inputting reference printed circuit board assembly data of the present invention, while FIG. 11 shows a sectional view through an exemplary reference printed circuit board assembly along with an output signal which is produced by a TV camera included in the FIG. 10 apparatus scanning said reference printed circuit board assembly.

This second preferred embodiment of the method for inputting reference printed circuit board assembly data of the present invention addresses itself to the following question, left unsatisfied in the case of the first preferred embodiment of the present invention. Namely, since a printed circuit board typically carries thereon wiring patterns, register marks, and other markings in addition to the component parts whose presence, positionings, and orientations are required to be checked, extracting only the data regarding these component parts from the other data that is inevitably produced during the teaching process is troublesome and time consuming, thereby causing a device for performing such extraction to be complex and expensive. Accordingly, a desire was felt for a way of avoiding this problem, and the second preferred embodiment of the method for inputting reference printed circuit board assembly data of the present invention was conceived of. This second preferred embodiment will now be described, with reference to FIGS. 10 and 11.

First, with regard to the setting up of the reference printed circuit board assembly P, shown in its finished aspect in FIG. 11, a layer of fluorescent adhesive tape A is laid over substantially the whole surface of a base printed circuit board PO, and then a layer B of transparent adhesive agent is coated over substantially the whole surface of said fluorescent tape layer A. Next, the reference component parts C are fitted to this base printed circuit board PO, i.e. are mounted in predetermined and appropriate positions and orientations on top of this layer B of transparent adhesive agent.

The fluorescent tape layer A is made of a material which glows strongly when exposed to ultraviolet radiation; or, in another possible implementation, said fluorescent tape layer A may be made of a material which glows strongly when exposed to visible light. Since the base printed circuit board PO and the reference component parts C mounted thereon are themselves typically made of materials which are slightly fluorescent by their nature, it is important that the fluorescent tape layer A should be made of a material which is, by contrast, strongly and intensely fluorescent by its nature, so that the image formed by a TV camera (as will be described shortly), included in an apparatus for automatic inspection of printed circuit board assemblies, of this base printed circuit board PO with the reference component parts C assembled thereto as shown in sectional view in FIG. 11 has good contrast, and is not deleteriously affected by ambient light conditions. It is also desirable that the layer B of transparent adhesive agent should be made from a material which is substantially transparent to the radiation which is emitted by the fluorescence of the fluorescent tape layer A.

In FIG. 10, there is shown a schematic block diagram of an apparatus for automatic inspection of printed circuit board assemblies which serves for the practice of this second preferred embodiment of the method for inputting reference printed circuit board assembly data of the present invention, by first taking a picture of the reference printed circuit board assembly P (as shown in FIG. 11) for setting up reference data, by subsequently taking a picture of a subject printed circuit board assembly (not particularly shown in the figures), and by then inspecting whether or not all of the reference component parts C are correspondingly mounted to the base printed circuit board PO, in this subject printed circuit board assembly, by checking the reference data against data similarly extracted from the picture of said subject printed circuit board assembly.

In this figure, the reference numeral 1 denotes a mercury lamp which serves as a light source, while 2 is a dichroic mirror which reflects the light from said mercury lamp 1 onto the subject printed circuit board assembly while also passing the light emitted from said subject printed circuit board assembly according to the fluorescence of the fluorescent tape layer A thereof upwards to a TV camera 3. This apparatus for automatic inspection of printed circuit board assemblies further includes an X-Y stage 4 which is arranged to be movable in the X and Y directions, on the upper surface of which in the figure the reference printed circuit board assembly or the subject printed circuit board assembly is mounted for being imaged by the TV camera 3. Also, there are included a processing unit 5, an input unit 6 for inputting a processing sequence when inputting the reference data from the reference printed circuit board assembly, and an output unit 7 which comprises a CRT, and printer, and the like for outputting records of the input sequences, the results of inspection, and so on.

The processing unit 5 comprises a central processing unit or CPU, a picture image processing unit for extracting the characteristic parameters for each of the component parts C mounted on the base printed circuit board by analog to digital converting the picture image signals from the TV camera 3, a drive unit for the X-Y stage 4, a memory for storing the characteristic parameters produced by said picture image processing unit and the input sequences which are inputted on the input unit 6, and another memory for storing the programs which are executed by the CPU; however, these internal details of this processing unit 5 are not particularly shown in the figure.

When this apparatus for automatic inspection of printed circuit board assemblies of the above described structure takes a picture of the reference printed circuit board assembly P of FIG. 11, then under the radiation from the mercury lamp 1 the fluorescent tape layer A of said reference printed circuit board assembly P glows by fluorescence, all over it except where said fluorescent glow is interrupted by the presence of the reference component parts C, and the TV camera 3 is thereby enabled to form a picture image which captures effectively and appropriately the contours of all such reference component parts C on the base printed circuit board PO, with the result that the output signal S of the TV camera 3, which is dispatched to the processing unit 5, will be a high precision picture image signal which has, as shown in FIG. 11, clearly defined highs where the reference component parts C are not present and clearly defined lows where said reference component parts C are present. In other words, the wiring pattern and the register marks and the other markings and so on which were originally present on the base printed circuit board PO are not distinguished by the TV camera 3 at this time, because said base printed circuit board PO is now covered over by the fluorescent tape layer A, but only the images of the reference component parts C are distinguished. Such distinguishing of said images of said reference component parts C is accordingly performed effectively and easily with relatively high resolution. The TV camera 3 is not required to be a relatively expensive color type TV camera, but may be a relatively inexpensive black and white TV camera.

According to the above described method of inputting reference data, if there are any omissions of the reference component parts C on the base printed circuit board PO, or if any of said reference component parts C are mis-positioned or mis-aligned or mis-oriented, this can easily be detected by monitoring the output of the CRT of the output unit 7, and these improperly arranged component parts C can be easily rearranged by the operator.

Further, there is an advantage in that the layer B of transparent adhesive agent can retain the reference component parts C onto the base printed circuit board PO and can prevent any shifting of said reference component parts C after they are mounted on said base printed circuit board PO. Accordingly, correction after the inputting of the position data to the inspection apparatus can be minimized.

The output signal of the TV camera 3 is analog to digital converted by the picture image processing unit of the processing unit 5 for the extraction of the reference characteristic parameters, consisting of the coordinates and the shapes of the reference component parts C mounted on the base printed circuit board PO, and these parameters are stored in the memory of the processing unit 5 as the reference data. Since the picture image that is formed by the TV camera 3 is only the silhouette or the outlines of the reference component parts C, this processing unit 5, and in particular its picture image processing unit, can be of an economical and efficient structure.

In the above described apparatus for automatic inspection of printed circuit board assemblies, it is recommended further to coat a preflux mixed with a fluorescent agent, in advance, over the subject base printed circuit board PO before mounting the subject component parts C thereon, and to mix a fluorescent agent into the solder cream for connecting said reference component parts C to the circuit pattern on the base printed circuit board PO and the bonding agent.

The determination process for each of the subject component parts C is performed by comparison of the area of the dark (non fluorescent) region representing each such subject component part C with the area given by the relevant reference parameters, in the case of checking whether or not one of such subject component parts C has been omitted; and by the detection of shifting of the shape and/or the center of gravity of said dark area representing each such subject component part C with that of the region given by the relevant reference parameters, in the case of checking whether or not one of such subject component parts C has been mis-positioned or mis-aligned or mis-oriented.

Although in this above described second preferred embodiment of the method for inputting reference printed circuit board assembly data of the present invention the fluorescent tape layer A was attached over the surface of the base printed circuit board PO for the reference printed circuit board assembly P, and then the layer B of transparent adhesive agent was coated over said fluorescent tape layer A, in another possible embodiment it would be possible, as an alternative, to coating a bonding agent mixed with a fluorescent agent over the base printed circuit board PO in advance, rather than using a tape layer A.

Summary

Thus, according to this second preferred embodiment of the method for inputting reference printed circuit board assembly data of the present invention, since the fluorescent tape layer A was attached over the surface of the base printed circuit board PO in the reference printed circuit board assembly P in advance, and then the layer B of transparent adhesive agent was coated over said fluorescent tape layer A, inputting of the reference data including the positions and the shapes of the reference component parts C was enabled to be accomplished in a short time with minimum effort, using a simple apparatus for automatic inspection of printed circuit board assemblies such as shown in FIG. 10.

Conclusion

Although the present invention has been shown and described in terms of the preferred embodiments thereof, and with reference to the appended drawings, it should not be considered as being particularly limited thereby, since the details of any particular embodiment, or of the drawings, could be varied without, in many cases, departing from the ambit of the present invention. Accordingly, the scope of the present invention is to be considered as being delimited, not by any particular perhaps entirely fortuitous details of the disclosed preferred embodiments, or of the drawings, but solely by the scope of the accompanying claims, which follow.

What is claimed is:

1. A method for automatic inspection of printed circuit board assemblies having component parts mounted on a base printed circuit board by processing an image which is obtained from said base printed circuit board mounted with said component parts and by inputting reference printed circuit board assembly data to an inspection step in said method, said method comprising the steps of:

preparing a reference base printed circuit board with reference component parts mounted thereon in which the visual distinction between said reference base printed circuit board and said reference component parts is clear;

obtaining an image from said reference base printed circuit board mounted with said reference component parts;

processing said image to obtain said reference printed circuit board assembly data, which contains information of predetermined characteristics of said reference component parts;

storing said reference printed circuit board assembly data; and inspecting said printed circuit board assemblies by obtaining an image therefrom, processing said image to obtain printed circuit board assembly data containing information of characteristics of the component parts mounted on said printed circuit board assemblies, inputting said reference printed circuit board assembly data and comparing the component part characteristics in the printed circuit board assembly data so obtained with the reference component part characteristics in the stored reference printed circuit board assembly data to determine acceptability of the printed circuit board assemblies, wherein said reference base printed circuit board is arranged to have low visual brightness, while said reference component parts are arranged to have high visual brightness.

2. A method for inspecting printed circuit board assemblies according to claim 1, wherein said reference base printed circuit board is arranged to be substantially black, while said reference component parts are arranged to be substantially white.

3. A method for inspecting printed circuit board assemblies according to claim 1, wherein said reference base printed circuit board is arranged to be substantially dark, while said reference component parts are arranged to be substantially bright.

4. A method for inspecting printed circuit board assemblies according to claim 3, wherein said reference base printed circuit board is arranged to be substantially black, while said reference component parts are arranged to be substantially white.

5. A method for automatic inspection of printed circuit board assemblies having component parts mounted on a base printed circuit board by processing an image which is obtained from said base printed circuit board mounted with said component parts and by inputting reference printed circuit board assembly data to an inspection step in said method, said method comprising the steps of:

preparing a reference base printed circuit board with reference component parts mounted thereon in which the visual distinction between said reference base printed circuit board and said reference component parts is clear;

obtaining an image from said reference base printed circuit board mounted with said reference component parts;

processing said image to obtain said reference printed circuit board assembly data, which contains information of predetermined characteristics of said reference component parts;

storing said reference printed circuit board assembly data; and inspecting said printed circuit board assemblies by obtaining an image therefrom, processing said image to obtain printed circuit board assembly data containing information of characteristics of the component parts mounted on said printed circuit board assemblies, inputting said reference printed circuit board assembly data and comparing the component part characteristics in the printed circuit board assembly data so obtained with the reference component part characteristics in the stored reference printed circuit board assembly data to determine acceptability of the printed circuit board assemblies, wherein said reference base printed circuit board is arranged to have high visual brightness, while said reference component parts are arranged to have low visual brightness.

6. A method for inspecting printed circuit board assemblies according to claim 5, wherein said reference base printed circuit board is coated with a colored film.

7. A method for inspecting printed circuit board assemblies according to claim 6, wherein said reference base printed circuit board is further coated with a layer of transparent adhesive agent over said layer of film.

8. A method for inspecting printed circuit board assemblies according to claim 6, wherein said layer of transparent adhesive agent further serves for retaining said reference component parts.

9. A method for inspecting printed circuit board assemblies according to claim 5, wherein said reference base printed circuit board is made to be fluorescent.

10. A method for inspecting printed circuit board assemblies according to claim 9, wherein said reference base printed circuit board is coated with a fluorescent film.

11. A method for inspecting printed circuit board assemblies according to claim 10, wherein said reference base printed circuit board is further coated with a layer of transparent adhesive agent over said layer of film.

12. A method for inspecting printed circuit board assemblies according to claim 10, wherein said layer of transparent adhesive agent further serves for retaining said reference component parts.

13. A method for automatic inspection of printed circuit board assemblies having component parts mounted on a base printed circuit board by processing an image which is obtained from said base printed circuit board mounted with said component parts and by inputting reference printed circuit board assembly data to an inspection step in said method, said method comprising the steps of:

preparing a reference base printed circuit board with reference component parts mounted thereon in which the visual distinction between said reference base printed circuit board and said reference component parts is clear;

obtaining an image from said reference base printed circuit board mounted with said reference component parts;

processing said image to obtain said reference printed circuit board assembly data, which contains information of predetermined characteristics of said reference component parts;

storing said reference printed circuit board assembly data; and inspecting said printed circuit board assemblies by obtaining an image therefrom, processing said image to obtain printed circuit board assembly data containing information of characteristics of the component parts mounted on said printed circuit board assemblies, inputting said reference printed circuit board assembly data and comparing the component part characteristics in the printed circuit board assembly data so obtained with the reference component part characteristics in the stored reference printed circuit board assembly data to determine acceptability of the printed circuit board assemblies, wherein said reference base printed circuit board is arranged to have substantially different color value from that of said reference component parts.

14. A method for inspecting printed circuit board assemblies according to claim 1, 13 or 5, wherein the characteristics pertain to the locations of the component parts and the reference component parts.

15. A method for inspecting printed circuit board assemblies according to claim 1, 13 or 5, wherein the characteristics pertain to the shapes of the component parts and the reference component parts.

* * * * *